US008609733B2

(12) United States Patent
Kohane et al.

(10) Patent No.: US 8,609,733 B2
(45) Date of Patent: *Dec. 17, 2013

(54) SENSORY-SPECIFIC LOCAL ANESTHESIA AND PROLONGED DURATION LOCAL ANESTHESIA

(75) Inventors: Daniel S. Kohane, Newton, MA (US); Itay Sagie, Haifa (IL)

(73) Assignees: Massachusetts Institute of Technology, Cambridge, MA (US); Children's Medical Center Corporation, Cambridge, MA (US)

( * ) Notice: Subject to any disclaimer, the term of this patent is extended or adjusted under 35 U.S.C. 154(b) by 247 days.

This patent is subject to a terminal disclaimer.

(21) Appl. No.: 12/993,622

(22) PCT Filed: May 19, 2009

(86) PCT No.: PCT/US2009/044549
§ 371 (c)(1),
(2), (4) Date: Nov. 19, 2010

(87) PCT Pub. No.: WO2009/143175
PCT Pub. Date: Nov. 26, 2009

(65) Prior Publication Data
US 2011/0086922 A1    Apr. 14, 2011

Related U.S. Application Data

(60) Provisional application No. 61/054,424, filed on May 19, 2008.

(51) Int. Cl.
*A01N 37/18* (2006.01)
*A61K 31/165* (2006.01)
*C07C 233/00* (2006.01)
*C07C 235/00* (2006.01)
*C07C 237/00* (2006.01)
*C07C 239/00* (2006.01)

(52) U.S. Cl.
USPC .......................................... 514/626; 564/193

(58) Field of Classification Search
USPC .......................................... 514/626; 564/193
See application file for complete search history.

(56) References Cited

U.S. PATENT DOCUMENTS

| 3,004,894 A | 10/1961 | Johnson |
| 3,328,259 A | 6/1967 | Anderson |
| 3,374,144 A | 3/1968 | Emmanuel |
| 4,537,776 A | 8/1985 | Cooper |
| 4,654,323 A | 3/1987 | Beitner |
| 4,820,720 A | 4/1989 | Sanders |
| 4,863,970 A | 9/1989 | Patel |
| 4,973,468 A | 11/1990 | Chiang |
| 5,006,342 A | 4/1991 | Cleary |
| 5,716,637 A | 2/1998 | Anselem |
| 6,326,020 B1 * | 12/2001 | Kohane et al. ................ 424/426 |
| 2002/0197284 A1 | 12/2002 | Luo |

FOREIGN PATENT DOCUMENTS

| EP | 0043738 | 1/1982 |
| GB | 2153223 | 8/1985 |
| WO | 8505621 | 12/1985 |
| WO | 9311798 | 6/1993 |
| WO | 0141550 | 6/2001 |
| WO | 2006091719 | 8/2006 |
| WO | 2008063603 | 5/2008 |

OTHER PUBLICATIONS

Scurlock et al. "Tetraethylammonium derivatives: Ulatralong-acting Local Anesthetics?" Anesthesiology, 1981,vol. 54,pp. 265-269.*
Lim et al. "The Quaternary Lidocaine Derivtive, QX-314, Produces Long-lasting Local Anesthesia in Animal Models In Vivo" Anesthesiology, 2007, vol. 107, pp. 305-311.*
Burdyga et al. "The effects of local anaesthetics on the electrical and mechanical activity of the guinea-pig ureter" Br. J. Pharmac., 1986, vol. 88, pp. 523-530.*
Taverna et al. "A Single Injection of Lidocaine as Local Anesthesia for Ultrasound Guided Needle Biopsy of the Prostate" The Journal of Urology, Jan. 2002, vol. 167, pp. 222-223.*
Adjei and Garren, "Pulmonary delivery of peptide drugs: effect of particle size on bioavailability of leuprolide acetate in healthy male volunteers" , Pharm. Res., 7:565-69 (1990).
Akerman, et al., "Penetration enhancers and other factors governing percutaneous local anaesthesia with lidocaine" , Acta Pharmacol. Toxicol.,45(1):58-65 (1979).
Binshtok, et al., "Inhibition of nociceptors by TRPV1-mediated entry of impermeant sodium channel blockers" , Nature, 449:607-610 (2007).
Choi and Maibach, "Liposomes and niosomes as topical drug delivery systems", J, Pharmacal and Biophys. Res.,18(5):209-19 (2005).
Cortesi, et al., "Sugar cross-linked gelatin for controlled release: microspheres and disks" , Biomaterials 19:1641-1649 (1998).
Fozzard, et al., "Mechanism of local anesthetic drug action on voltage-gated sodium channels" , Curr. Pharm. Des., 11:2671-2686 (2005).
Kohane, et al., "A re-examination of tetrodotoxin for prolonged duration local anesthesia" , Anesthesiology, 89:119-31 (1998A).
Kohane, et al., "Sciatic nerve blockade in infant, adolescent, and adult rats: a comparison of ropivacaine with bupivacaine" , Anesthesiology, 89:1199-1208 (1998B).
Masters, at al., "Prolonged regional nerve blockade by controlled release of local anesthetic from a biodegradable polymer matrix" , Anesthesiology, 79(2):340-346 (1993).

(Continued)

*Primary Examiner* — Kendra D Carter
(74) *Attorney, Agent, or Firm* — Pabst Patent Group LLP

(57) ABSTRACT

Combinations of charged local anesthetics with chemical permeation enhancers have been developed to give long duration block which is selective for sensory block over motor block. The duration of block is greatly prolonged by combining the local anesthetic with a permeation enhancer. The selectivity of sensory over motor block is provided by selecting the concentration of the local anesthetic and the permeation enhancer to provide selective permeability of the sensory and motor neurons to the enhancer.

30 Claims, 8 Drawing Sheets

(56) References Cited

OTHER PUBLICATIONS

McLure and Rubin, "Review of local anaesthetic agents", Minerva Anesthesiol., 71:59-74 (2005).
Padrea, et al., "Tetrodotoxin for prolonged local anesthesia with minimal myotoxicity", Muscle Nerve, 34:747-53 (2006).
Ruetsch., et al., "From cocaine to ropivacaine: the history of local anesthetic drugs", Curr. Top. Med. Chem., 1:175-182 (2001).
Scholz, "Mechanisms of (local) anaesthetics on voltage-gated sodium and other ion channels", Br J. Anaesth., 89:52-61 (2002).
Zanen, et al., "The optimal particle size for parasympathicolytic aerosols in mild asthmatics", J. Int. J. Pharm., 114: 111-115 (1995).

* cited by examiner

QX-314 [mM]

OTAB [mM] (with constant QX-314 25mM)

QX-314 [mM] (with constant OTAB 30mM)

US 8,609,733 B2

SENSORY-SPECIFIC LOCAL ANESTHESIA AND PROLONGED DURATION LOCAL ANESTHESIA

CROSS REFERENCE TO RELATED APPLICATIONS

This application is a national phase filing under 35 U.S.C. §371 of PCT/US2009/044549 filed under the Patent Cooperation Treaty on May 19, 2009, which claims priority to and benefit of U.S. Provisional Patent Application No. 61/054,424, filed on May 19, 2008, by Daniel S. Kahane, Itay Sagie and Emmanuel J. Simons, the contents of these applications are hereby incorporated by reference in their entirety.

GOVERNMENT SUPPORT

This invention was made with government support under Grant No. GM073626 awarded by National Institute of General Medical Sciences. The government has certain rights in the invention.

FIELD OF THE INVENTION

The present invention relates to formulations or methods that provide prolonged local anesthesia with sensory specificity.

BACKGROUND OF THE INVENTION

Local anesthetics are drugs that can produce a reversible loss of sensation when applied to nerve tissues. They interfere with the conduction process of the nerve tissues by blocking use-dependent voltage-gated $Na^+$ channels and thus inhibit initiation and propagation of action potentials of the nerve tissues. At present, more than ten types of local anesthetics are in use, including, for example, bupivacaine, lidocaine, cocaine, mepivacaine, tetracaine, and ropivacaine. These drugs can be cataloged into esters and amides according to their metabolic processes, in which the former type is metabolized mainly in the blood through hydrolysis by esterases whereas the latter type is metabolized in the liver. In terms of pharmacological mechanism, these two types of local anesthetics both achieve effects of infiltrative cutaneous anesthesia, peripheral nerve blocking, and spinal/epidural anesthesia through $Na^+$ channel blocking (McLure, et al. (2005), *Minerva Anesthesiol.*, 71:59-74 (2005); Scholz, *Br J. Anaesth.*, 89:52-61 (2002); Fozzard, et al., *Curr. Pharm. Des.*, 11:2671-2686 (2005); Ruetsch, et al. (2001), *Curr. Top. Med. Chem.*, 1:175-182 (2001).

When applied locally to a nerve tissue in appropriate concentrations, local anesthetics reversibly block the action potentials responsible for nerve conduction. Local anesthetics act on any part of the nervous system and on every type of nerve fiber. Thus, a local anesthetic in contact with a nerve trunk can cause both sensory and motor paralysis in the area enervated. Therefore, although the goal of topical or regional anesthesia is to block the transmission of signals in nociceptors to prevent pain, the administration of local anesthetics also produces numbness from block of low-threshold pressure and touch receptors, paralysis from block of motor axons, and block of autonomic fibers. A strategy for generating pain-restricted local anesthesia while preserving motor and autonomic responses is desirable in conditions such as childbirth, some dental procedure or in treating nociceptor-driven chronic pain such as postherptic neuralgia. Sensory-specific nerve block has been achieved in the prior art by using capsaicin in conjunction with the quaternary lidocaine derivative QX-314 (Clifford, et al., *Nature*, 449:607-610 (2007)). Thus, there is still a need for compositions that provide sensory-specific nerve block.

It is therefore an object of the invention to provide a formulation for local anesthesia that is selective for sensory blockade.

It is still another object of the invention to provide a method of local anesthesia that is selective for sensory blockade.

SUMMARY OF THE INVENTION

Combinations of charged local anesthetics with chemical permeation enhancers have been developed to give long duration block which is selective for sensory block over motor block. The duration of block is greatly prolonged by combining the local anesthetic with a permeation enhancer. The selectivity of sensory over motor block is provided by selecting the concentration of the local anesthetic and the permeation enhancer, as well as the chemical nature of the surfactant, to provide selective permeability of the sensory and motor neurons to the enhancer, as demonstrated by the examples.

Combinations of charged local anesthetics such as lidocaine and lidocaine derivatives with chemical permeation enhancers (CPE) give long duration sensory selective block. In one embodiment, the duration of block is greatly prolonged by combining an amount of the local anesthetic with an amount of a CPE such as TWEEN™ (polysorbate) that is effective to selectively prolong the duration of sensory block, without commensurate (or any) increase in the duration of motor block.

DETAILED DESCRIPTION OF THE INVENTION

I. Definitions

Figure 1:
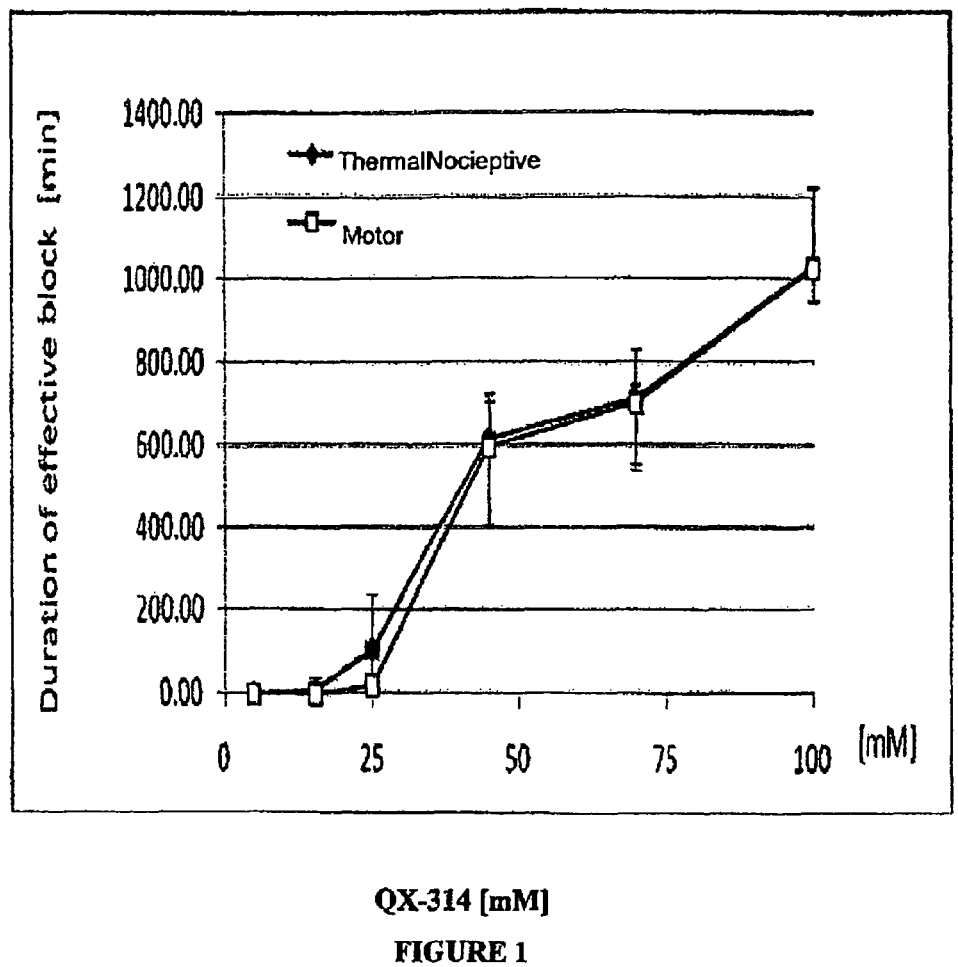
FIG. 1 is a line graph showing the effect of different concentrations (0, 15, 25, 50, 75, and 100 mM) of QX-314 on the duration of effective block ("DEB") for sensory (-♦-) and motor (-■-) block. The DEB are shown as medians with the $25^{th}$ and $75^{th}$ percentiles. (n=4) (n=8 for all except QX-314 25 mM n=20 and QX-314 15 mM n=4).

As used herein, chemical penetration enhancer (CPE) denotes any agent which can alter a biological barrier to enhance permeant flux.

As used herein, local anesthetic (LA) refers to any agent that produces nerve blockade within a specific area, region or site.

"Aryl", as used herein, refers to -, 6- and 7-membered aromatic, heterocyclic, fused aromatic, fused heterocyclic, biaromatic, or biheterocyclic ring system, optionally substituted by halogens, alkyl-, alkenyl-, and alkynyl-groups. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, carbazolyl, carbolinyl, chromenyl, chromenyl, cinnolinyl, decahydroquinolinyl, 2H,6H-1,5,2-dithiazinyl, dihydrofuro[2,3 b]tetrahydrofuran, firanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, pyrrolidinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2, 4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., C1-C30 for straight chain, C3-C30 for branched chain), preferably 20 or fewer carbons, more preferably 10 or fewer carbons, most preferably 5 or fewer carbons. Likewise, preferred cycloalkyls have from 3-10 carbon atoms in their ring structure, and more preferably have 5, 6 or 7 carbons in the ring structure. The alkyl group can be substituted with one or more substituents including, but not limited to, alkyl, aryl, halogen, hydroxy, and thiol.

II. Compositions

The composition is designed to produce sensory-specific local anesthesia, and to prolong the duration of block of a charged local anesthetic. The formulations consist of a local anesthetic such as lidocaine or lidocaine derivative, in combination with one or more chemical penetration enhancers, including, but not limited to, surfactants, terpenes, amino amides, amino esters, azide-like compounds and alcohols in a suitable pharmaceutically acceptable carrier. The concentration of the chemical penetration enhancer in the composition is effective to selectively prolong the duration of sensory block, without any effect on motor block, which can be determined as demonstrated by the examples. The preferred formulation contains the lidocaine derivative QX-314. The formulation is administered locally at the site where the nerve is to be blocked, preferably as a solution.

A. Local Anesthetics

Useful local anesthetics include amino-amide or amino-ester local anesthetics, any at least partly amphiphilic local anesthetic, local anesthetics that act not on the surface of the cell, and any at least partly charged local anesthetic. Some of these local anesthetics have some degree of sensory selectivity in the absence of a CPE.

In one embodiment, the local anesthetic is a charged local anesthetic, preferably a permanently charged local anesthetic. Preferred charged local anesthetics are those of Formula I or Formula II:

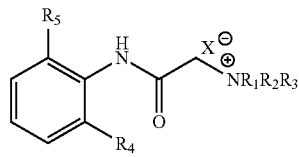

Formula I

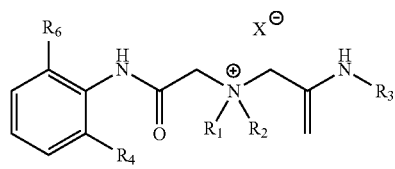

Formula II where $R_1$-$R_5$ are independently selected from hydrogen; linear, branched, or cyclic alkyl and aryl groups.

Suitable local charged anesthetics of Formula I and II include, but are not limited to, charged lidocaine derivatives, such as QX-314 ((N-(2,6)dimethylphenylcarbamoylmethyl triethylammonium bromide); QX-222 (2-((2,6-dimethylphenyl)amino)-N,N,N-trimethyl-2-oxoethanaminium); QX-572 (N,N-bis(phenylcarbamoylmethyp-dimethylammonium chloride).

QX-314 is a quaternary lidocaine derivative that is permanently charged and lipophobic. QX-314 is a powerful blocker of voltage-sensitive Na+ conductance when applied intracellularly. QX-314 suppresses the generation of Na+-dependent spikes from inside the cell membrane, without affecting Ca2+ currents or glutamate-activated currents. Other suitable charged anesthetics include, but are not limited to, tonicaine.

The structures of QX-314, QX-222, QX-572, and tonicaine are shown below:

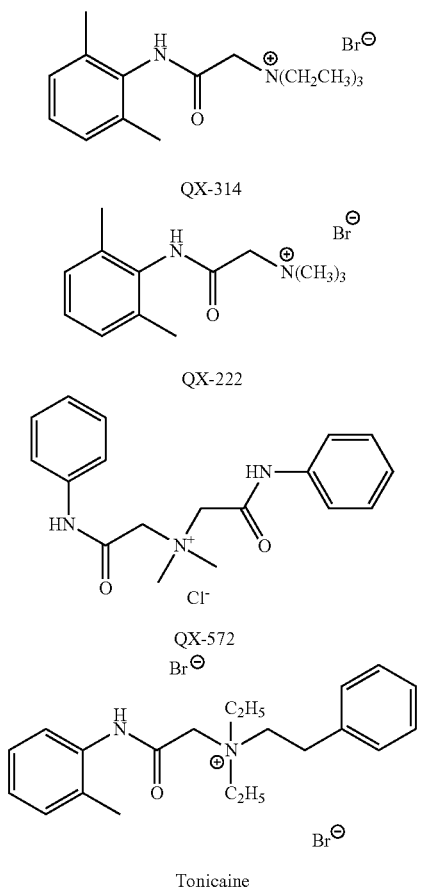

Other suitable charged local anesthetics include, but are not limited to, charged tetracaine derivatives (e.g., N-butyl tetracaine) and permanently charged derivatives of flecainide.

In one embodiment, the local anesthetic is in an excipient having a pH that causes the local anesthetic to be charged.

B. Chemical Penetration Enhancers

Numerous compounds have been evaluated for penetration enhancing activity, including sulphoxides (e.g., dimethylsulfoxide ("DMSO") and decylmethylsulfoxide (C10MSO)), Azones (e.g. laurocapram), pyrrolidones (for example 2-pyrrolidone, 2P), alcohols and alkanols (ethanol, or decanol), glycols (for example, propylene glycol, PG, a common excipient in topically applied dosage forms), surfactants (also common in dosage forms) and terpenes.

Suitable penetration enhancers include sulfoxide decylmethylsulfoxide ($C_{10}$MSO); ethers such as diethylene glycol monoethyl ether, dekaoxyethylene-oleylether, and diethylene glycol monomethyl ethers; surfactants such as sodium lauryl sulfate (SLS), sodium octyl sulfate (SOS), dodecyltriethylammonium bromide (DDAB), octyltriethylammonium bromide (OTAB), TWEEN® 20 and TWEEN® 80, fatty acids such as C8-C22 and other fatty acids, C8-C22 fatty alcohols, and polyols.

In the preferred embodiment, the CPEs are surfactants. Representative categories of surfactants include anionic surfactants, such as sodium lauryl sulfate (SLS) and sodium octyl sulfate (SOS); cationic surfactants, such as dodecyltriethylammonium bromide (DDAB) and octyltriethylammonium bromide (OTAB); and nonionic surfactants, such as TWEEN® 20 and TWEEN® 80. Preferred CPEs are listed along with some of their properties in

TABLE 1

| Properties of the chemical penetration enhancers (CPEs). | | |
|---|---|---|
| CPE | MW | Length of Carbon Chain |
| Sodium Octyl Sulfate (SOS) | 232.28 | 8 |
| Sodium Dodecyl Sulfate (SLS) | 288.38 | 12 |
| Octyl-trimethyl-ammonium Bromide (OTAB) | 252.23 | 8 |
| Dodecyl-trimethyl-ammonium Bromide (DDAB) | 308.34 | 12 |
| Tween ® 20 (TW 20) | 1228 | 12 |
| Tween ® 80 (TW 80) | 1310 | 17 |

These CPEs have the chemical structures provided in Table 2.

TABLE 2

| Structures for preferred CPEs | |
|---|---|
| CPE/CLASS | Structure |
| SOS Anionic | (structure shown) |

TABLE 2-continued

Structures for preferred CPEs

| CPE/CLASS | Structure |
|---|---|
| SLS Anionic | 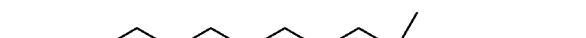 |
| OTAB Cationic | 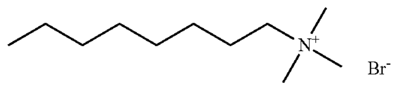 |
| DDAB Cationic | 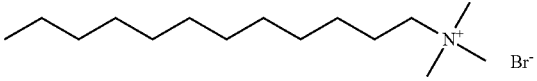 [SMILES: CCCCCCCCCCCC[N+](C)(C)C ; [Br-]] |
| TW 20 Nonionic | 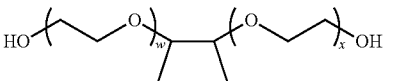<br>$w + x + y + z = 20$ |
| TW 80 Nonionic | <br>$w + x + y + z = 20$ |

Other suitable penetration enhancers include, but are not limited to, urea, (carbonyldiamide), imidurea, N, N-diethylformamide, N-methyl-2-pyrrolidine, 1-dodecal-azacyclopheptane-2-one, calcium thioglycate, 2-pyyrolidine, N,N-diethyl-m-toluamide, oleic acid and its ester derivatives, such as methyl, ethyl, propyl, isopropyl, butyl, vinyl and glycerylmonooleate, sorbitan esters, such as sorbitan monolaurate and sorbitan monooleate, other fatty acid esters such as isopropyl laurate, isopropyl myristate, isopropyl palmitate, diisopropyl adipate, propylene glycol monolaurate, propylene glycol monooleatea and non-ionic detergents such as BRIJ® 76 (stearyl poly(10 oxyethylene ether), BRIJ® 78 (stearyl poly(20)oxyethylene ether), BRIJ® 96 (oleyl poly(10)oxyethylene ether), and BRIJ® 721 (stearyl poly (21) oxyethylene ether) (ICI Americas Inc. Corp.). Fatty acids such as linoleic acid, capric acid, lauric acid, and neodecanoic acid, which can be in a solvent such as ethanol or propylene glycol, can be used as lipid bilayer disrupting agents. Vegetable oils, such as peanut oil, may also be used as a penetration enhancer U.S. Pat. No. 4,537,776 to Cooper contains a summary of prior art and background information detailing the use of certain binary systems for permeant enhancement. European Patent Application 43,738, also describes the use of selected diols as solvents along with a broad category of cell-envelope disordering compounds for delivery of lipophilic pharmacologically-active compounds. A binary system for enhancing metaclopramide penetration is disclosed in UK Patent Application GB 2,153,223 A, consisting of a monovalent alcohol ester of a C8-32 aliphatic monocarboxylic acid (unsaturated and/or branched if C18-32) or a C6-24 aliphatic monoalcohol (unsaturated and/or branched if C14-24) and an N-cyclic compound such as 2-pyrrolidone or N-methylpyrrolidone.

Combinations of enhancers consisting of diethylene glycol monoethyl or monomethyl ether with propylene glycol monolaurate and methyl laurate are disclosed in U.S. Pat. No. 4,973,468 for enhancing the transdermal delivery of steroids such as progestogens and estrogens. A dual enhancer consisting of glycerol monolaurate and ethanol for the transdermal delivery of drugs is described in U.S. Pat. No. 4,820,720. U.S. Pat. No. 5,006,342 lists numerous enhancers for transdermal drug administration consisting of fatty acid esters or fatty alcohol ethers of $C_2$ to $C_4$ alkanediols, where each fatty acid/alcohol portion of the ester/ether is of about 8 to 22 carbon atoms. U.S. Pat. No. 4,863,970 discloses penetration-enhancing compositions for topical application including an active permeant contained in a penetration-enhancing vehicle containing specified amounts of one or more cell-envelope disordering compounds such as oleic acid, oleyl alcohol, and glycerol esters of oleic acid; a $C_2$ or $C_3$ alkanol and an inert diluent such as water.

Liposomes are microscopic aggregates if highly ordered lipid molecules which are normally dispersed in a hydrophilic solvent. Liposomes have been shown to enhance the permeability of drugs (reviewed in Choi, et al., *J. Pharmacol and Biophys. Res.*, 18(5):209-19 (2005). In another embodiment, suspensions in chromophores conventionally used in the art to enhance permeation are used. The local anesthetic can also be administered as an emulsion, such as an oil-in-water or a water-in-oil emulsion.

C. Combinations of Anesthetic and CPE

The local anesthetic and CPE can be combined into a single dosage form or sequentially administered. The effective amount and ratio of CPE to anesthetic is dependent on the anesthetic, the CPE, the site of administration, and the species into which the anesthetic is administered. More specifically, dosage and concentrations will change depending on the size of nerve, species, anatomic location (peripheral nerve, epidural space, intrathecal), and even the volume of injectate. The concentration and dosages can be determined as demonstrated in the examples.

In another embodiment, these agents are co-injected with a vanilloid receptor agonist, a vasoconstrictor, or a site I channel blocker such as tetrodotoxin (TTX), saxitoxin (STX), decarbamoyl saxitoxin, neosaxitoxin, or gonyautoxin.

D. Formulations

The compounds described herein can be formulated for parenteral or topical formulation. The compounds can be combined with one or more pharmaceutically acceptable carriers and/or excipients that are considered safe and effective and may be administered to an individual without causing undesirable biological side effects or unwanted interactions. The carrier is all components present in the pharmaceutical formulation other than the active ingredient or ingredients.

Parenteral Formulations

The compounds described herein can be formulated for parenteral administration. "Parenteral administration", as used herein, means administration by injection.

The preparation of an aqueous composition that contains one or more of the compounds described herein is known in the art. Typically, such compositions can be prepared as injectable formulations, for example, solutions or suspensions; solid forms suitable for using to prepare solutions or suspensions upon the addition of a reconstitution medium prior to injection, emulsions, such as water-in-oil (w/o) emulsions, oil-in-water (o/w) emulsions, and microemulsions thereof, liposomes, and emulsomes (see U.S. Pat. No. 5,716,637 to Anselem et al.).

The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. In many cases, it will be preferable to include isotonic agents, for example, sugars or sodium chloride.

Solutions of the active compounds as the free acid or base or pharmacologically acceptable salts thereof can be prepared in water suitably mixed with one or more pharmaceutically acceptable excipients including, but not limited to, surfactants, dispersants, emulsifiers, pH modifying agents, and combination thereof. Dispersions also can be prepared in glycerol, liquid polyethylene glycols, and mixtures thereof and in oils, such as vegetable oils, e.g., peanut oil, corn oil, sesame oil, etc. Dispersions can contain one or more of the pharmaceutically acceptable excipients listed above.

Suitable surfactants to facilitate formulation may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate; glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

Under ordinary conditions of storage and use, the formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

Controlled Release Formulations

The parenteral formulations described herein can be formulated for controlled release including immediate release, delayed release, extended release, pulsatile release, and combinations thereof. The compositions can be incorporated into microparticles, nanoparticles, or combinations thereof that provide controlled release. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the body by means including enzymatic degradation and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to, hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

In some cases, it may be desirable to alter the rate of water penetration into the microparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropylcellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins which are water insoluble, such as zein, can also be used as materials for the formation of drug containing microparticles. Additionally, proteins, polysaccharides and combinations thereof which are water soluble can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. Detailed descriptions of these processes can be found in "Remington—The science and practice of pharmacy", 20th Edition, Jennaro et. al., (Phila, Lippencott, Williams, and Wilkens, 2000).

For some carrier materials it may be desirable to use a solvent evaporation technique to produce drug containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin (Cortesi, R., et al., *Biomaterials* 19 (1998) 1641-1649). Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water soluble protein can be spray coated onto the microparticles and subsequently cross-linked by the one of the methods described above. Alternatively, drug containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

Injectable/Implantable Solid Implants

The compositions described herein can be incorporated into injectable/implantable solid implants, such as polymeric implants. In one embodiment, the compositions are incorporated into a polymer that is a liquid or paste at room temperature, but upon contact with aqueous medium, such as physiological fluids, exhibits an increase in viscosity to farm a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication require polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the compositions can be incorporated into a polymer matrix and molded or compressed into a device that is a solid at room temperature. For example, the compositions can be incorporated into a biodegradable polymer, such as polyanhydrides and copolymers thereof, polyhydroalkanoic acids and copolymers thereof, PLA, PGA, and PLGA, and compressed into solid device, such as disks, or extruded into a device, such as rods.

Topical Formulations

Suitable dosage forms for topical administration include creams, ointments, salves, sprays, gels, lotions, emulsions, and transdermal patches. The formulation may be formulated for transmucosal, transepithelial, transendothelial, or transdermal administration.

"Emollients" are an externally applied agent that softens or soothes skin and are generally known in the art and listed in compendia, such as the "Handbook of Pharmaceutical Excipients", 4$^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl pahnitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

"Hydrophilic" as used herein refers to substances that have strongly polar groups that readily interact with water.

"Lipophilic" refers to compounds having an affinity for lipids.

"Amphiphilic" refers to a molecule combining hydrophilic and lipophilic (hydrophobic) properties "Hydrophobic" as used herein refers to substances that lack an affinity for water; tending to repel and not absorb water as well as not dissolve in or mix with water.

A "gel" is a colloid in which the dispersed phase has combined with the continuous phase to produce a semisolid material, such as jelly.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, C12-C15 alkyl benzoates, mineral oil, squalane, cyclomethicone, capric/caprylic triglycerides, and combinations thereof.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

The term aerosol as used herein refers to any preparation of a fine mist of particles, which can be in solution or a suspension, whether or not it is produced using a propellant. Aerosols can be produced using standard techniques, such as ultrasonication or high pressure treatment. See, for example, Adjei, A. and Garren, J. Pharm. Res., 7: 565-569 (1990); and Zanen, P. and Lamm, J.-W. J. Int. J. Pharm., 114: 111-115 (1995). Preferably, the aqueous solutions is water, physiologically acceptable aqueous solutions containing salts and/or buffers, such as phosphate buffered saline (PBS), or any other aqueous solution acceptable for administration to a animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydofuran, ethyl ether, and propanol may be used for the formulations. The solvent is selected based on its ability to readily aerosolize the formulation. The solvent should not detrimentally react with the compositions. An appropriate solvent should be used that dissolves the compositions or forms a suspension of the compositions. The solvent should be sufficiently volatile to enable formation of an aerosol of the solution or suspension. Additional solvents or aerosolizing agents, such as freons, can added as desired to increase the volatility of the solution or suspension.

III. Methods of Administration

The composition can be administered by any of the methods for administering local anesthetics known to one of ordinary skill in the art. The composition can be formulated for topical anesthesia, infiltration anesthesia, filed block anesthesia, nerve block anesthesia, intravenous regional anesthesia, spinal anesthesia and epidural anesthesia. The local anesthetic drug is selected based on the method of administration. The composition is used when it is desirable to retain motor function without pain.

The use of such local anesthesia enhancement could be used in epidural treatments for painless delivery, without compromising the motor abilities of the woman giving birth; post operative healing would be much more comfortable, allowing a painless recovery without motor disabilities.

EXAMPLES

Example 1

Effect of a Cationic Surfactant on the Duration and Selectivity of Nerve blockade by a Local Anesthetic.

Materials and Methods:

Animal Care

Young adult male Sprague-Dawley rats (350-420 g) were obtained from Charles River Laboratories (Wilmington, Mass.) and housed in groups of two per cage on a 6 a.m. to 6 p.m. light/dark cycle. All animals were cared for in accordance with protocols approved institutionally and nationally.

Chemical Enhancers & Solution Preparation

QX-314 and octyltriethylammonium bromide (OTAB) (Sigma) solutions were prepared in saline individually and in combination with each enhancer the night before scheduled injections.

Sciatic Blockade Technique

Animals were cared for in compliance with protocols approved by the Massachusetts Institute of Technology (MIT) Committee on Animal Care, in conformity with the NIH guidelines for the care and use of laboratory animals (NIH publication #85-23, revised 1985). Rats were anesthetized using isoflurane in oxygen. A 25-gauge needle was introduced posteromedial to the greater trochanter, and 300 μL of the QX-314+/−enhancer solution was injected upon contacting bone. To determine the effect of QX-314 on sensory and motor blockade, animals were injected with QX-314 at different concentrations. To determine the effect of the chemical penetration enhancer (OTAB) on the sensory and motor blockade produced by QX-314, animals were injected with different concentrations of OTAB, with the concentration of QX-314 kept constant at 25 mM.

Assessment of Nerve Blockade

In all experiments, the experimenter was blinded as to what treatment any given rat had received. Presence and extent of nerve blockade was investigated as previously described (Kohane, et al., *Anesthesiology,* 89:1199-1208 (1998); Padera, et al., *Muscle Nerve,* 34:747-53 (2006); Kohane, et al., *Anesthesiology,* 89:119-31 (1998); Masters, et al., *Anesthesiology,* 79(2):340-346 (1993)). Briefly, thermal nociception of each leg was assessed, with the right (uninjected) leg serving as an untreated control.

Thermal nociception was assessed by a modified hotplate test. Hind paws were exposed in sequence (left then right) to a 56° C. hot plate (Model 39D Hot Plate Analgesia Meter, IITC Inc., Woodland Hills, Calif.). The time (latency) until paw withdrawal was measured with a stopwatch. If the animal did not remove its paw from the hot plate within 12 seconds, it was removed by the experimenter to avoid injury to the animal or the development of hyperalgesia.

The duration of thermal nociceptive block was calculated as the time required for thermal latency to return to a value of 7 seconds from a higher value. Seven seconds is the midpoint between a baseline thermal latency of approximately 2 seconds in adult rats and a Maximal latency of 12 seconds. Latencies greater than 7 sec were considered to be effective blocks.

Extensor Postural Thrust (EPT)

The rat was held with its posterior placed at a digital balance on which it could bear weight with one hindpaw at a time. The maximum weight that the rat could bear without its ankle touching the balance was measured.

Results:

Effect of QX-314 on the Duration of Effective Thermal Nociceptive and Motor Block FIG. 1 shows the concentration-dependent sensory and motor blockade produced by QX-314 in the absence of a CPE. Injection of 300 μl of QX-314 at the sciatic nerve resulted in a concentration-dependent increase in both sensory and motor duration of block, with no evidence of modality specificity.

Effect of OTAB at Different Concentrations on the Duration and Selectivity of Nerve Blockade A low concentration of QX-314 (25 mM) co-injected with increasing concentrations of OTAB demonstrated a sensory-specific increase in block duration (FIG. 2A). At lower concentrations of OTAB (10-30 mM), there was significant increase in sensory block duration, without a corresponding increase in motor block duration. The duration of sensory and motor block from QX-314 alone was 165 minutes (FIG. 1). When co-injected with 20 mM OTAB, however, the sensory DEB from QX-314 increased to 428 minutes, and with 30 mM OTAB, the duration of sensory block was 450 min. There was little or no motor effect at these concentrations of OTAB. At higher OTAB concentrations (>30 mM), however, no sensory specificity was found, indicating there is a window of CPE concentrations in which domain specificity is achievable.

Figure 2A:
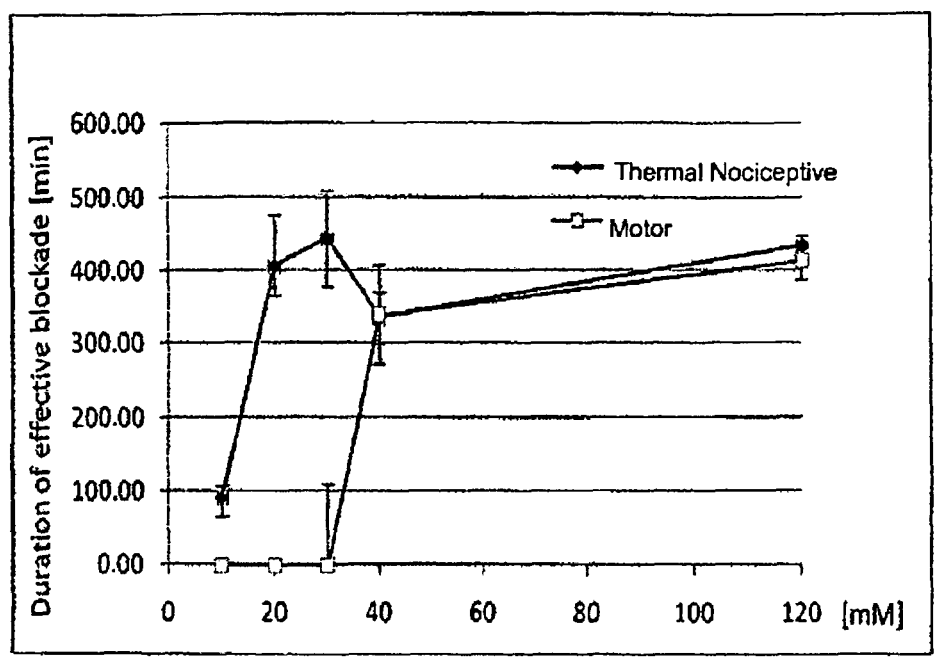
FIG. 2A is a line graph showing the effect of different concentrations of octyltriethylammonium bromide (OTAB) on the duration of effective sensory (-♦-) and motor (-■-) block ("DEB") produced by 25 mM QX-314. The DEB are shown as medians with the $25^{th}$ and $75^{th}$ percentiles. (n=6,20, 10,4,4 for OTAB 10 mM, 20 mM, 30 mM, 40 mM and 120 mM respectively).
Figure 2B:
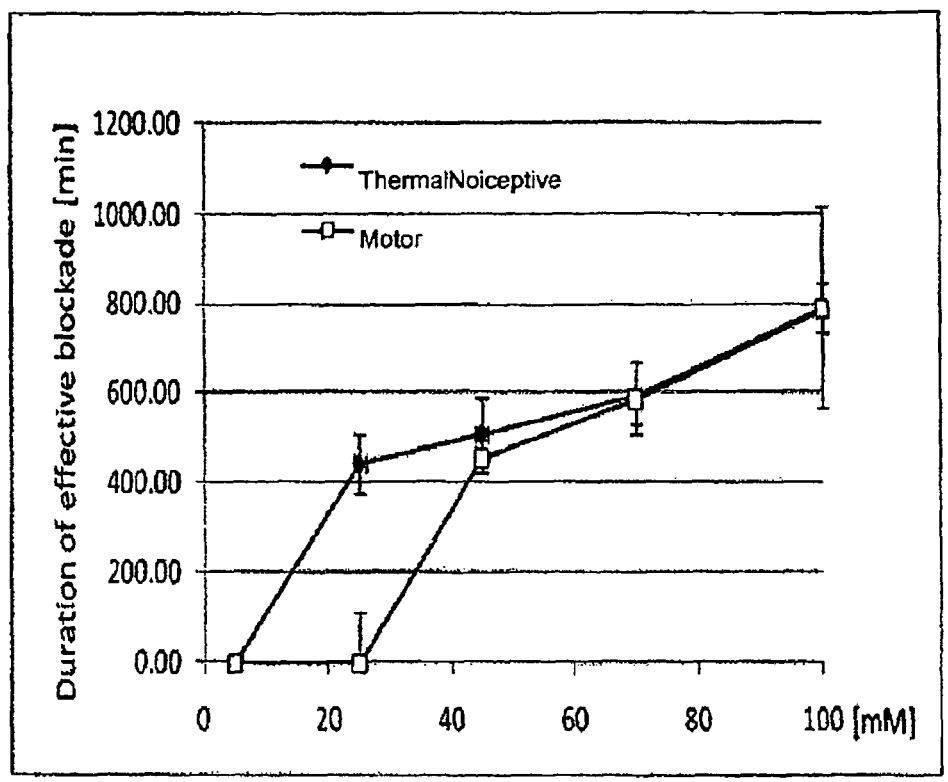
FIG. 2B is a line graph showing the effect of 30 mM OTAB on the duration of effective sensory (-♦-) and motor (-■-) block ("DEB") produced by different concentrations of QX-314 (5-100 mM). The DEB are shown as medians with the $25^{th}$ and $75^{th}$ percentiles. n4 for all except 25 mM QX-314 n=10.

FIG. 2B shows that sensory selectivity at 30 mM OTAB was also dependent on concentration of QX-314, with greatest selectivity between 10 and 40 mM QX-314.

Example 2

Effects of Anionic and Non-Ionic Surfactants on the Duration and Selectivity of Nerve Blockade by a Local Anesthetic Materials and Methods:
Methods were as described in Example 1.
Results:
Effect of TWEEN® 20 on Nerve Blockade Using QX-314

Figure 3A:
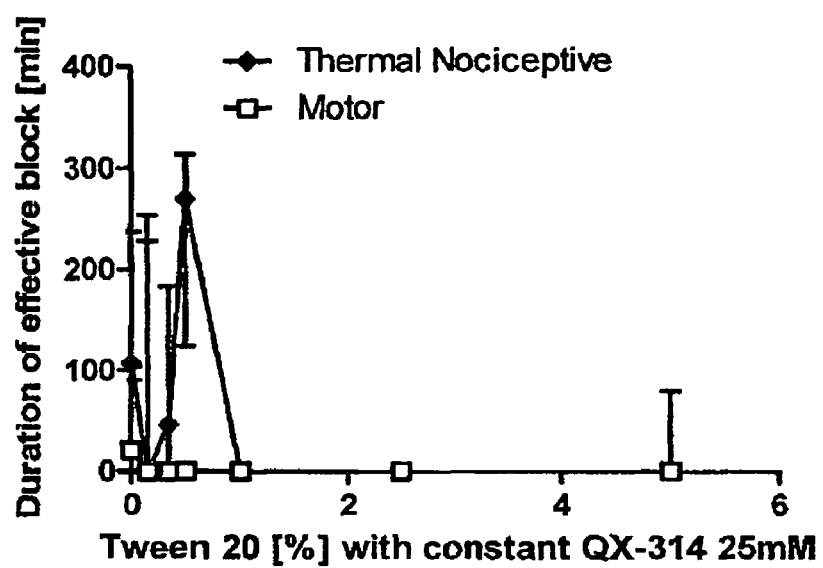
FIG. 3A is a line graph showing the effect of different concentrations of TWEEN® 20 (0%, 0.15%, 0.35%, 0.5% and 1%, 2.5%, 5%) on the duration of nerve blockade for sensory (-■-) and motor (-□-) block produced by 25 mM QX-314. The durations of block are shown as medians with the $25^{th}$ and $75^{th}$ percentiles (n=8).

In order to investigate whether or not this sensory specific phenomenon is exclusive to the cationic OTAB, two additional surfactants from different families (anionic and non-ionic) were chosen. When co-injected with QX-314 (25 mM), TWEEN® 20 (polysorbate 20) (a non-ionic CPE) was shown to have a window of concentrations in which a sensory specific nerve blockade is observed. This "window" is between 0.35% and 1% TWEEN® 20 with the maximum sensory specificity at 0.5% giving a median of 269 minutes of sensory blockade and 0 minutes of motor blockade (FIG. 3A). The duration of this sensory blockade is more than twice as long as the duration of sensory blockade from 25 mM QX-314 alone (107 min) (FIG. 1) and is about half as long as the sensory specific blockade from 25 mM QX-314 with 20 mM OTAB (406 min) (FIG. 2A).

Figure 3B:
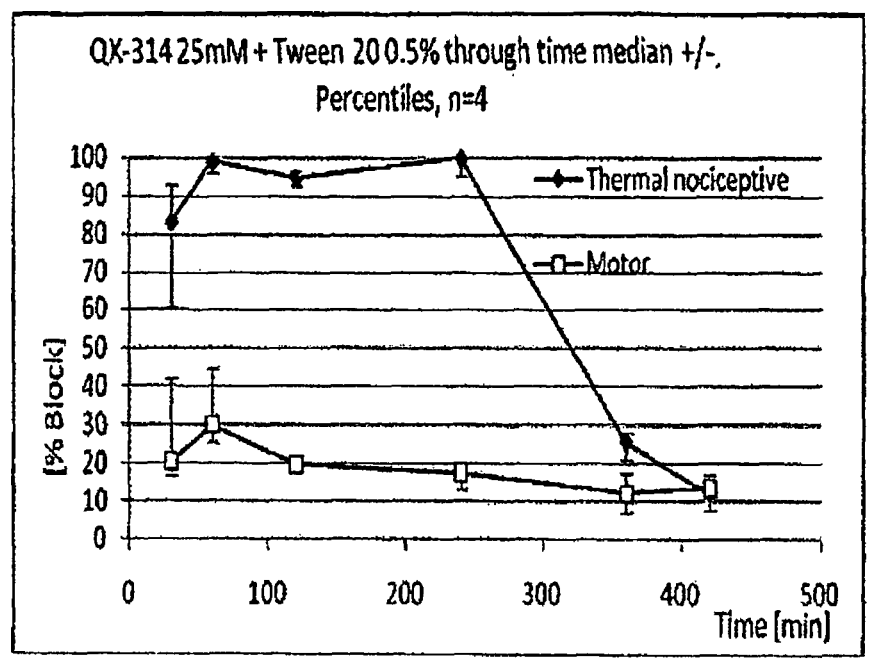
FIG. 3B is a graph of % block over time (minutes) for QX-314 25 mM with TWEEN® 20 0.5%.

FIG. 3B is a graph of % block over time (minutes) for QX-314 25 mM with TWEEN® 20 0.5%.

Effect of SOS on Nerve Blockade from QX-314

Figure 4A:
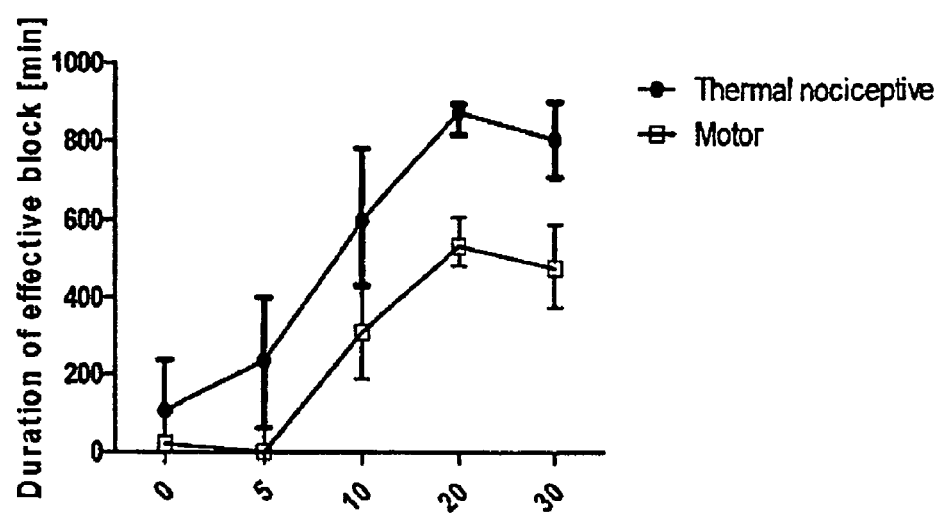
FIG. 4A is a line graph showing the effect of different concentrations of sodium octyl sulfate (SOS) (0, 5, 10, 20 and 30 mM) on the duration of nerve blockade ("DEB") for sensory (-●-) and motor (-□-) block produced by 25 mM QX-314. The DEB are shown as medians with the 25$^{th}$ and 75$^{th}$ percentiles (n =4).
Figure 4B:
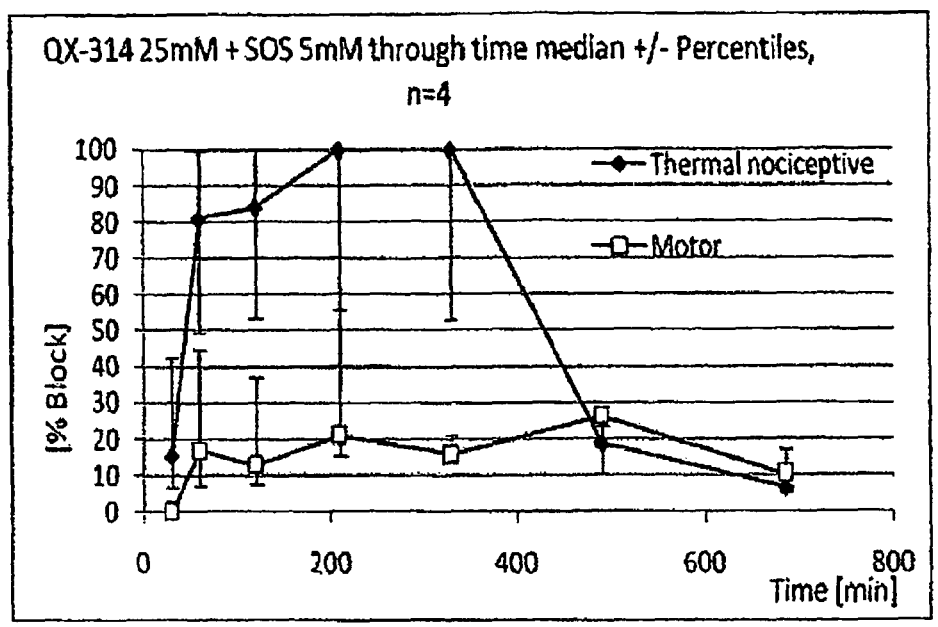
FIG. 4B is a graph of % block over time (minutes) for QX-314 25 mM with SOS 5 mM.

Sensory specific nerve blockade was also tested using sodium octyl sulfate (SOS), an anionic chemical penetration enhancer. A similar "window" of sensory specific nerve blockade was observed using this CPE. When co-injected with 25 mM QX-314 sensory selectivity at all concentrations of SOS (5, 10, 20, 30 mM) was observed. (FIG. 4A) For example, when co-injecting 25 mM QX-314 with 10 mM SOS, 870 minutes and 532 minutes of sensory and motor block were achieved, respectively. However, when 5 mM SOS was co-injected with 25 mM QX-314, 235 minutes and 0 minutes of sensory and motor block were achieved, respectively (FIG. 4B). This is more than twice the duration of sensory block achieved when injecting 25 mM QX-314 alone.

In summary,
With 25 mM QX-314, there is sensory selectivity with:
OTAB: 10 mM-30 mM, 20 mM is optimal.
SOS: 1-50 mM. At 5 mM there is sensory specificity. At higher concentrations (10-30 mM), block is initially non-specific.

TWEEN® 20: 0.15%- 1%, the optimal concentration is 0.5%

Example 3

Demonstration of Selective Block with OTAB and QX-222

Figure 5:
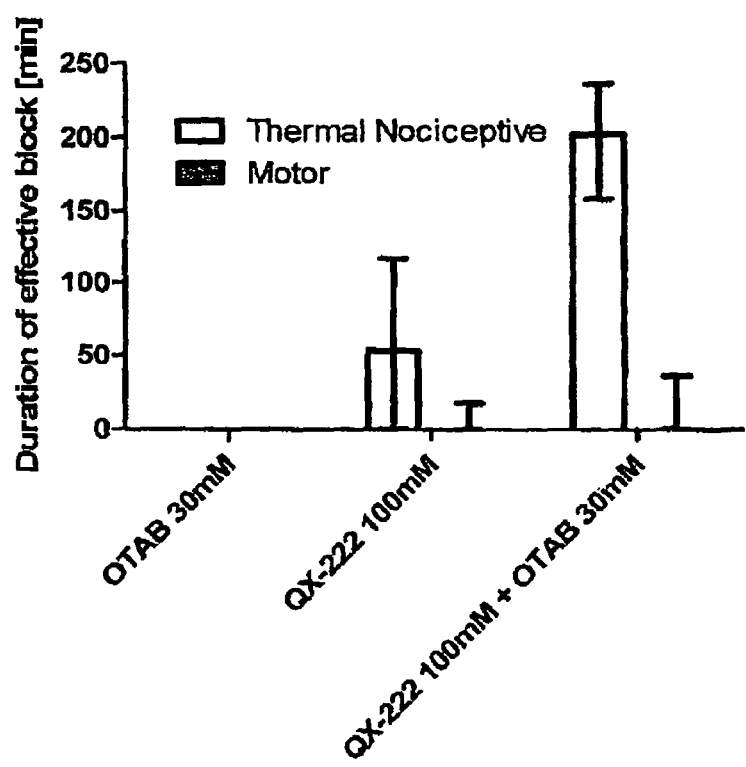
FIG. 5 is a graph of the effect of 30 mM OTAB on the duration of effective motor (light grey) and thermal nociceptive (white) block (minutes) from 100 mM QX-222.

Materials and Methods
To establish that the selective block could be obtained with other local anesthetics, the methods of example 1 were performed using 100 mM QX-222 and 30 mM OTAB, and compared to the results obtained using 100 mM QX-222 and 30 mM OTAB.
Results
The results are shown in FIG. 5. Comparable selective thermal nociceptive blockade as compared to motor blockade was obtained with both QX-314 and QX-222 in combination with OTAB.

Modifications and variations of the present invention are intended to come within the scope of the following claims.

We claim:
1. A method for selective sensory nerve blockade comprising administering a combination of effective amounts of a charged local anesthetic selected from the group consisting of local anesthetics of Formula I:

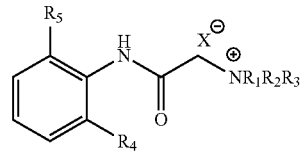

Formula I where $R_1$-$R_5$ are independently selected from linear or branched alkyl groups, and
a chemical permeation enhancer selected from the group consisting of sulfoxide decylmethylsulfoxide ($C_{10}$MSO); diethylene glycol monoethyl ether, dekaoxyethylene-oleylether, diethylene glycol monomethyl ethers; sodium lauryl sulfate (SLS), sodium octyl sulfate (SOS), dodecyltriethylammonium bromide (DDAB), octyltriethylammonium bromide (OTAB), and polysorbate,
in a suitable pharmaceutically acceptable carrier to selectively increase or prolong the duration of sensory block, without affecting motor block.

2. The method of claim 1 wherein the local anesthetic comprises an excipient having a pH rendering the local anesthetic charged.

3. The method of claim 1 further comprising administering the local anesthetic and chemical permeation enhancer with a vasoconstrictor.

4. The method of claim 1 wherein the local anesthetic is selected from the group of QX-314((N-(2,6)dimethylphenyl-carbamoylmethyl triethylammonium bromide); and QX-222 (2-((2,6-dimethylphenyl)amino)-N,N,N-trimethyl-2-oxoethanaminium).

5. The method of claim 1 wherein the chemical penetration enhancer is sodium lauryl sulfate (SLS), sodium octyl sulfate (SOS), dodecyltriethylammonium bromide (DDAB), or octyltriethylammonium bromide (OTAB).

6. The method of claim 1 wherein the chemical permeation enhancer is selected from the group consisting of polysorbate 80 and polysorbate 20.

7. The method of claim 1 wherein the local anesthetic and chemical permeation enhancer are administered as a bolus dosage unit.

8. The method of claim 1 wherein the local anesthetic and chemical permeation enhancer are administered in a continuous or sustained release formulation.

9. The method of claim 1 wherein the local anesthetic and chemical permeation enhancer are administered in a topical or aerosol formulation.

10. The method of claim 1 wherein the local anesthetic and chemical permeation enhancer is administered by injection.

11. A composition for selective sensory nerve blockade comprising a combination of effective amounts of a charged local anesthetic selected from the group consisting of local anesthetics of Formula I:

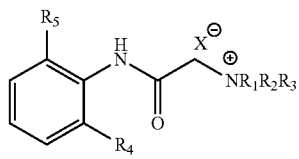

Formula I where $R_1$-$R_5$ are independently selected from linear or branched alkyl groups, and a chemical permeation enhancer selected from the group consisting of sulfoxide decylmethylsulfoxide ($C_{10}MSO$); diethylene glycol monoethyl ether, dekaoxyethylene-oleylether, diethylene glycol monomethyl ethers; sodium lauryl sulfate (SLS), sodium octyl sulfate (SOS), dodecyltriethylammonium bromide (DDAB), octyltriethylammonium bromide (OTAB), and polysorbate, in a suitable pharmaceutically acceptable carrier to selectively increase or prolong the duration of sensory block, without affecting motor block.

12. The composition of claim 11 wherein the local anesthetic comprises an excipient having a pH rendering the local anesthetic charged.

13. The composition of claim 11 further comprising administering the local anesthetic and chemical permeation enhancer with a vasoconstrictor.

14. The composition of claim 11 wherein the local anesthetic is a selected from the group of QX-314((N-(2,6)dimethylphenylcarbamoylmethyl triethylammonium bromide); and QX-222 (2-((2,6-dimethylphenyl)amino)-N,N,N-trimethyl2-oxoethanaminium).

15. The composition of claim 11 wherein the chemical penetration enhancer is sodium lauryl sulfate (SLS), sodium octyl sulfate (SOS), dodecyltriethylammonium bromide (DDAB), or octyltriethylammonium bromide (OTAB).

16. The composition of claim 11 wherein the chemical permeation enhancer is selected from the group consisting of polysorbate 80 and polysorbate 20.

17. The composition of claim 11 in a bolus dosage unit.

18. The composition of claim 11 in a continuous or sustained release formulation.

19. The composition of claim 11 in a topical or aerosol formulation.

20. The composition of claim 11, wherein the pH of the formulation is from about 3 to about 8.

21. The composition of claim 20, wherein the pH of the composition is about 4.5 to about 7.5.

22. The composition of claim 11, further comprising an effective amount of a site I sodium channel blocker.

23. The composition of claim 22 wherein the site I sodium channel blocker is saxitoxin, decarbamoyl saxitoxin, or neosaxitoxin.

24. The composition of claim 23 wherein the local anesthetic is an amino-amide or amino-ester local anesthetics or derivatives thereof.

25. The composition of claim 23 wherein the site I sodium channel blocker is neosaxitoxin and the local anesthetic is QX-314.

26. The method of claim 1, further comprising administering an effective amount of a site I sodium channel blocker.

27. The method of claim 26, wherein the site I sodium channel blocker is saxitoxin, decarbamoyl saxitoxin, or neosaxitoxin.

28. The method of claim 27 wherein the site I sodium channel blacker is neosaxitoxin and the local anesthetic is QX-314.

29. The method of claim 1 wherein the pH of the composition is from about 3 to about 8.

30. The method of claim 1 wherein the pH is from about 4 to about 7.5.

* * * * *